(12) United States Patent
DeLuca et al.

(10) Patent No.: US 6,480,731 B1
(45) Date of Patent: Nov. 12, 2002

(54) BIOMEDICAL ELECTRODE

(75) Inventors: Carlo J. DeLuca, Wellesley, MA (US); L. Donald Gilmore, Wellesley, MA (US)

(73) Assignee: Altec, Inc., Boston, MA (US)

( * ) Notice: Subject to any disclaimer, the term of this patent is extended or adjusted under 35 U.S.C. 154(b) by 0 days.

(21) Appl. No.: 09/668,982

(22) Filed: Sep. 25, 2000

Related U.S. Application Data

(62) Division of application No. 09/192,949, filed on Nov. 16, 1998, now Pat. No. 6,129,666.

(51) Int. Cl.⁷ .................................................. A61B 5/04
(52) U.S. Cl. ........................ 600/393; 600/546; 607/152
(58) Field of Search .............................. 600/372, 373, 600/374, 391, 392, 393; 607/152

(56) References Cited

U.S. PATENT DOCUMENTS 4,852,572 A * 8/1989 Nakahashi et al. ......... 600/393
5,938,597 A * 8/1999 Stratbucker ................. 600/393

* cited by examiner

Primary Examiner—Michael Peffley
Assistant Examiner—David M. Ruddy
(74) Attorney, Agent, or Firm—John E. Toupal; Harold G. Jarcho

(57) ABSTRACT

A biomedical electrode including a flexible pad having a top surface and a bottom surface; an asymmetrical, linearly aligned array of signal contacts retained by the flexible pad and each having a contact surface projecting from the bottom surface and a coupling surface projecting above the top surface; and a connector including a plurality of connector contacts each being shaped and arranged for electrical connection to a different one of the coupling surfaces. The asymmetrical array of signal contacts facilitates proper positioning of the electrode on the skin.

19 Claims, 6 Drawing Sheets

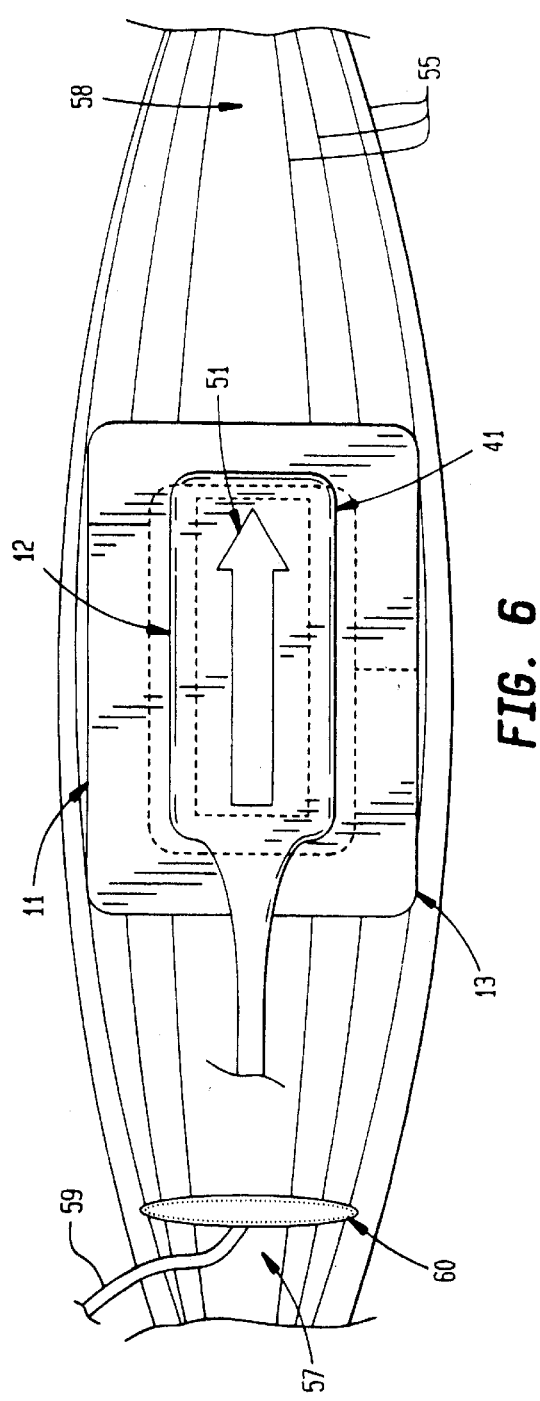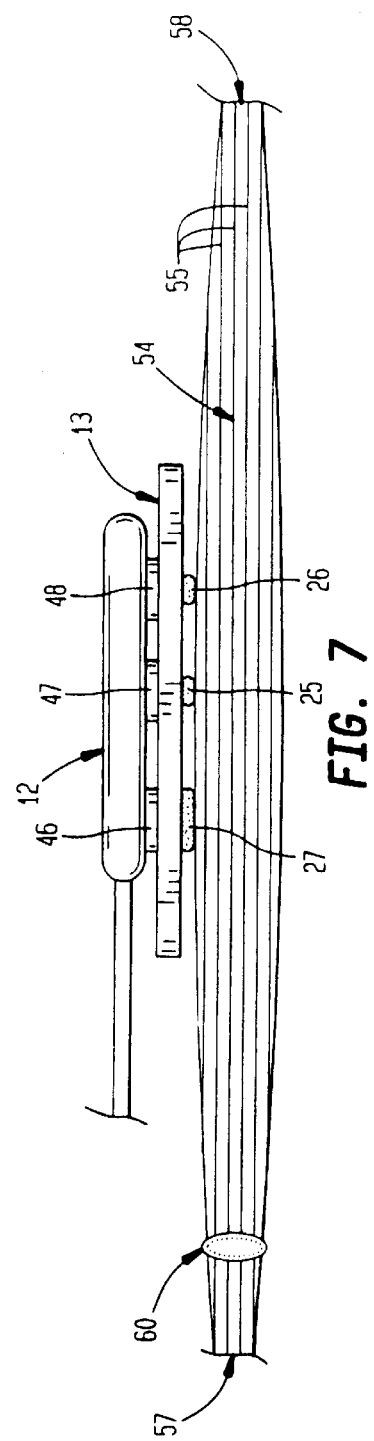

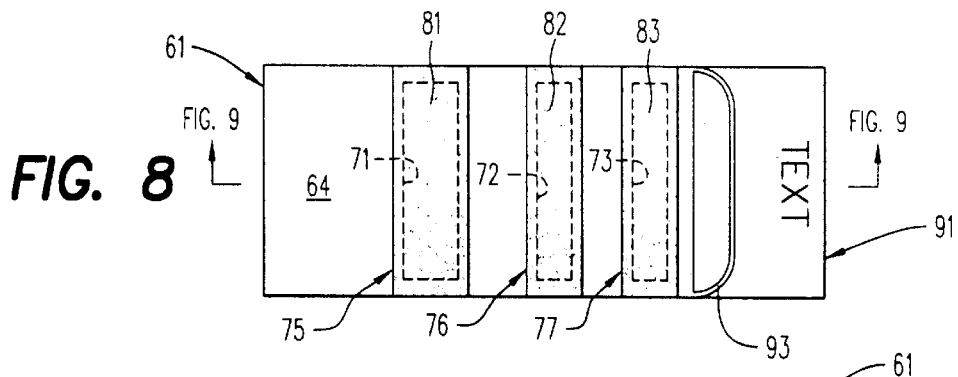
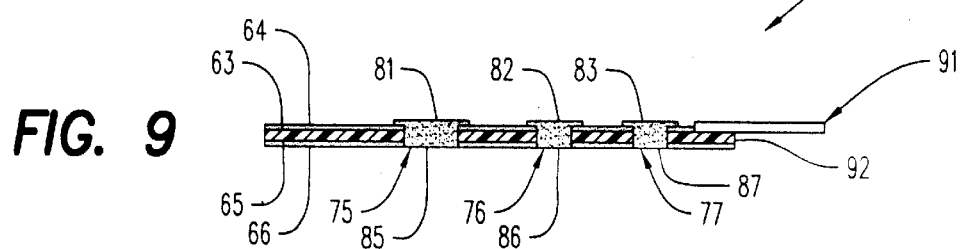
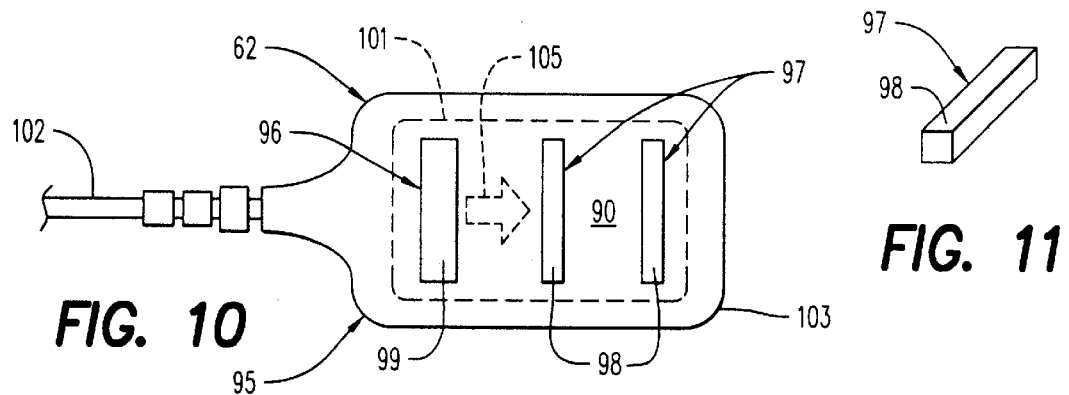
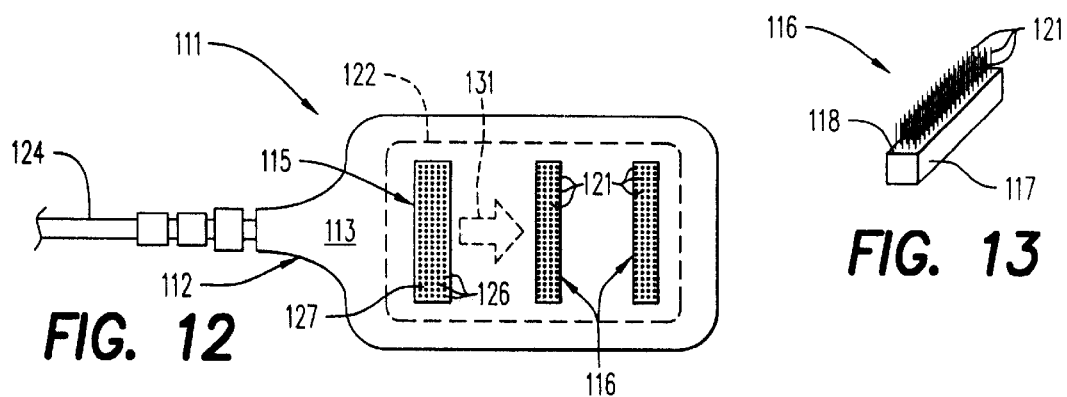

BIOMEDICAL ELECTRODE

This application is a Divisional of application Ser. No. 09/192,949 filed on Nov. 16, 1998 Now U.S. Pat. No. 6,129,666.

BACKGROUND OF THE INVENTION

This invention relates generally to a biomedical electrode and, more particularly, to a disposable biomedical electrode for establishing electrical contact between a skin portion of the human anatomy and electrical diagnostic equipment.

Many types of disposable biomedical electrodes are known. Typically they comprise an electrically-conductive terminal member having means for electrical connection to electromedical equipment, an adhesive tape or pad for holding the terminal member in place on the skin; and an electrically-conductive, conformable interfacing material such as an electrolyte gel or paste over the surface of the terminal member which contacts the skin to reduce skin impedance and improve electrical contact between the skin and the terminal member. Although prior electrodes function in many applications, they suffer a variety of individual and collective deficiencies such as being difficult to properly orient on the body and failing to provide signals with consistent, repeatable amplitude and frequency parameters.

SUMMARY OF THE INVENTION

The invention is a biomedical electrode including a flexible pad having a top surface and a bottom surface; an asymmetrical, linearly aligned array of signal contacts retained by the flexible pad and each having a contact surface projecting from the bottom surface and a coupling surface projecting above the top surface; and a connector including a plurality of connector contacts each being shaped and arranged for electrical connection to a different one of the coupling surfaces. The asymmetrical array of signal contacts facilitates proper positioning of the electrode on the skin.

According to one feature of the invention, the connector further comprises a substrate retaining the connector contacts in an asymmetrical, linearly aligned array geometrically matching the array of signal contacts. The matching arrays facilitate interconnection of the connector contacts and coupling surfaces.

According to other features of the invention, the substrate is a case retaining an amplifier interconnected with the connector contacts, each of the coupling surfaces is defined by a snap contact, each of the connector contacts is a receptacle for receiving one of the snap contacts, and each of the signal contact surfaces is formed by a gel substance. These features provide an efficient, easily employed electrode system.

According to yet another feature of the invention, the bottom surface of the pad is adhesive to facilitate attachment of the electrode to the skin.

According to an additional feature, the electrode includes indicia disposed on the pad and indicating, with respect to an adjacent bundle of muscle fibers, a desired linearly directed orientation for the array of signal contacts.

According to a further feature, the electrode includes indicia disposed on the substrate and indicating, with respect to an adjacent bundle of muscle fibers, a desired linearly directed orientation for said array of connector contacts.

According to other features of the invention, the indicia comprises directional indicators disposed, respectively, on the top surface and the substrate.

According to an additional feature of the invention, the flexible pad includes first and second portions divided by perforations adapted to facilitate separation thereof. The first and second portions can be selectively separated to reduce the size of the electrode for certain applications.

According to still other features of the invention, the first portion is a central portion and retains the signal contacts and the second portion is a marginal portion surrounding the central portion. With this arrangement, the separated central portion functions as a complete electrode.

According to another feature of the invention, the contact surfaces have areas of different size. This feature facilitates the formation of contact surfaces which exhibit desirable equal current density.

According to features of another embodiment, a biomedical electrode includes a flexible pad with adhesive top and bottom surfaces and a linear array of slots, a conductive gel contact retained in each slot and having a contact surface forming a portion of the bottom surface and a coupling surface forming a portion of the top surface, and a connector with connector contacts arranged to engage the coupling surfaces. The adhesive surfaces facilitate assembly of the pad between the connector and a muscle to be monitored.

According to features of yet another embodiment, a biomedical electrode consists of a flexible connector having an adhesive substrate; a plurality of connector contacts projecting from the substrate, each contact formed by a plurality of conductive bristles; and a flexible amplifier retained by the connector and interconnected with the contacts. The flexible connector can be positioned directly on skin covering a muscle to be monitored and the conductive bristles project through hair to insure good electrical contact.

DESCRIPTION OF THE DRAWINGS

These and other objects and features of the invention will become more apparent upon a perusal of the following description taken in conjunction with the accompanying drawings wherein:

FIG. 6 is a schematic top view of the electrode of FIG. 1 mounted adjacent to a bundle of muscle fibers;

FIG. 7 is a side view of the electrode and muscle fiber bundle shown in FIG. 6;

FIG. 8 is a plan view of another pad embodiment of the invention;

FIG. 9 is a side elevational view of the pad shown in FIG. 8;

FIG. 10 is a plan view of a connector for use with the pad illustrated in FIGS. 8 and 9;

FIG. 11 is a perspective view of a contact used with the connector of FIG. 10;

FIG. 12 is a plan view of another biomedical electrode embodiment of the invention;

FIG. 13 is a perspective view of a contact used with the electrode of FIG. 12;

DESCRIPTION OF THE PREFERRED EMBODIMENT

Figure 1:
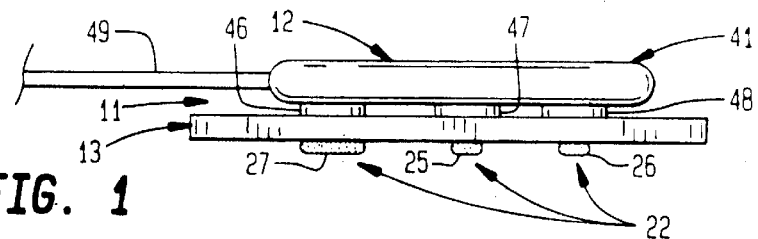
FIG. 1 is an elevational view of a biomedical electrode according to the invention.
Figure 2:
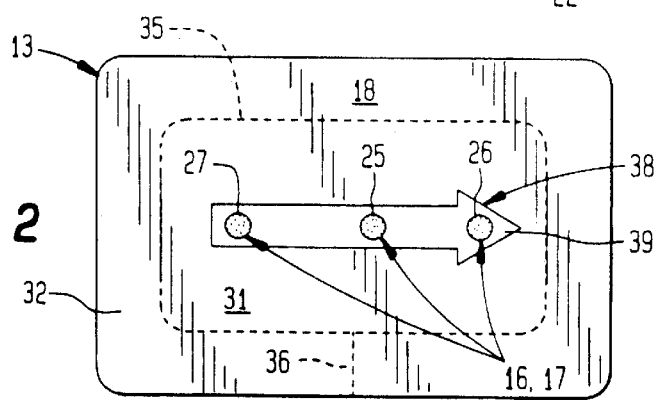
FIG. 2 is a top view of a pad component of the electrode shown in FIG. 1.
Figure 3:
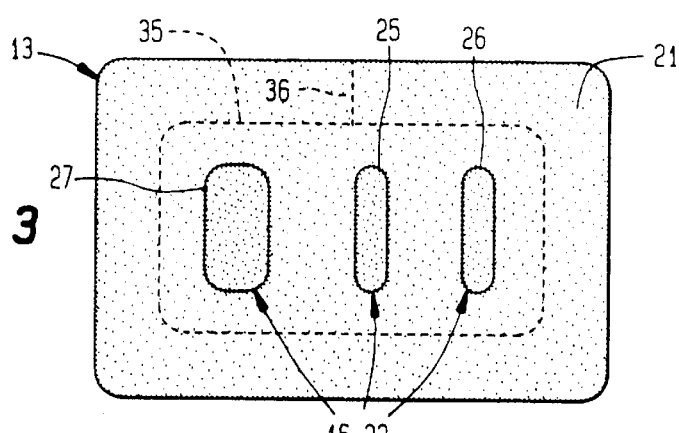
FIG. 3 is a bottom view of the pad shown in FIG. 2.

A biomedical electrode 11 includes a connector 12 and a flexible foam pad 13 illustrated in FIG. 1. As shown in FIGS. 2 and 3, the pad 13 retains an asymmetrical, linearly aligned array of signal contacts 16. Each of the signal contacts 16 has a button snap portion forming a coupling surface 17 that projects above a top surface 18 of the pad 13. Projecting from a bottom surface 21 of the pad 13 are contact surfaces 22 of the signal contacts 16. Each of the contact surfaces 22 is formed with a suitable, electrically conductive gel material and the bottom surface 21 is provided with suitable adhesiveness. Included among the signal contacts 16 are a pair of detection contacts 25, 26 (FIG. 3) which have contact surfaces of equal area and a reference contact 27 which has a contact surface area substantially equal to the sum of the areas of the contact surfaces of the detection contacts 25, 26. Asymmetry for the array of signal contacts 16 is established by providing a larger spacing between the reference contact 27 and the detector contact 25 than between the detector contacts 25, 26.

A first central portion 31 of the pad 13 is divided from a second marginal portion 32 thereof by annular perforations 35. An additional line of perforations 36 extend between the annular perforations 35 and an outer edge of the pad 13. The perforations 35, 36 facilitate tearing of the pad 13 to separate the first and second portions 31, 32 thereof. As shown in FIGS. 2 and 3, all of the signal contacts 16 are retained by the first central portion 31 of the pad 13. Disposed on the top surface 18 of the pad 13 is indicia 38 in the form of an arrow 39 aligned with the linear array of signal contacts 16 and pointed from the reference contact 27 toward the detection contacts 25, 26.

Figure 4:
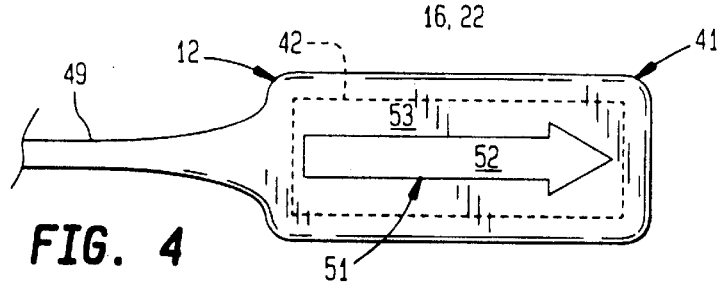
FIG. 4 is a top view of a connector component of the electrode shown in FIG. 1.
Figure 5:
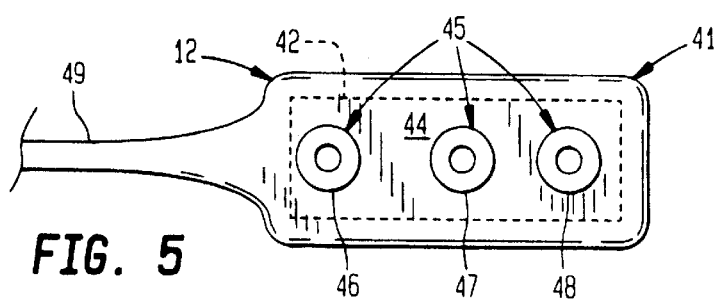
FIG. 5 is a bottom view of the connector shown in FIG. 4.

The connector 12 (FIGS. 4 and 5) includes a molded case 41 that retains a preamplifier 42. Disposed on a bottom substrate surface 44 of the case 41 is an asymmetrical, linearly aligned array of connector contacts 45 interconnected with the preamplifier 42. Included among the connector contacts 45 are a reference connector contact 46 and a pair of detector connector contacts 47, 48. Each of the connector contacts 45 is a cylindrical receptacle shaped for press fitted engagement with one of the signal contact coupling surfaces 17 on the top surface 18 of the pad 13. The array of connector contacts 45 geometrically match the array of signal contacts 16 so as to facilitate interconnection thereof. Extending from the molded case 41 is an electrical cable 49 interconnected with the preamplifier 42 and the connector contacts 45. Connector indicia 51 in the form of an arrow 52 is disposed on a top surface 53 of the connector case 41. The arrow 52 is aligned with the linear array of connector contacts 45 and points in a direction from the reference connector contact 46 toward the detector connector contacts 47, 48.

Prior to use of the electrode 11, the connector 12 is attached to the pad 13 by press fitting the button snaps 17 into the connector contact receptacles 45. Next, the adhesive bottom surface 21 of the pad 13 is adhered to the skin of a test subject adjacent to a bundle 54 of muscle fibers 55 as shown in FIGS. 6 and 7. Alternatively, the pad 13 first can be fixed on a test subject and then attached to the connector 12. Proper mating of the connector contacts 45 and signal contacts 16 is insured by the asymmetry of the contact arrays. Either one or both of the arrows 38, 52 is used to properly orient the electrode 11 with respect to the muscle fibers 55. Proper orientation aligns the arrows 39, 52 with the fibers 55 of the bundle 54 and pointed in a direction from a proximal end 57 toward a distal end 58 of the bundle 55. The proximal end 57 is located adjacent to an innervation zone 60 established at a terminal portion of a nerve 59. That arrangement of the electrode 11 establishes a known positive potential for the detector contact 25 and a negative potential for the detector contact 26.

Illustrated in FIGS. 8–11 is another biomedical electrode consisting of a flexible pad 61 shown in FIGS. 8 and 9 and a connector 62 shown in FIGS. 10 and 11. The pad 61 has a top surface 63 with a portion covered by an adhesive layer 64 and a bottom surface 65 with a portion covered by an adhesive layer 66. Extending through the pad 61 are three linearly arranged, parallel slots 71–73 with elongated rectangular cross-sections. Each of the slots 71–7 is filled with a conductive gel that forms, respectively, a reference signal contact 75 and a pair of detection signal contacts 76, 77. Provided by the signal contacts 75–77 are, respectively, elongated coupling surfaces 81–83 which form portions of the top surface 63 project above and transversely beyond top edges of the slots 71–73. Also provided by the signal contacts 75–77 are, respectively, elongated contact surfaces 85–87 that form portions of the bottom surface 65 and are aligned with the adhesive layer 66. As in the electrode embodiment 11, the contact surface 85 has an area substantially equal to the sum of the areas of the contact surfaces 86 and 87.

A tab 91 is attached to one end 92 of the top surface. Retained by the upper surface of the tab 91 is alignment indicia in the form of a line 93 having a pre-determined shape. The function of the indicia 93 is described below. Also retained by the tab 91 is instructional text explaining proper use of the electrode 61.

The connector portion 62 of the electrode consists of a molded case 95 with a bottom surface 90 supporting a linear array of connector contacts including a reference connector contact 96 and a pair of detector connector contacts 97. As illustrated in FIG. 11, the detector connector contacts 97 are electrically conductive blocks having exposed, elongated rectangular contact surfaces 98 that align with the detector coupling surfaces 82, 83 of the pad 61. The reference connector contact 96 also is a block but with a larger rectangular contact surface 99 that aligns with the reference coupling surface 81 of the pad 61. Retained within the case 95 is a flexible preamplifier 101 connecting the reference connector contact 96 and the detector contacts 97 to a cable 102 connectable to suitable analysis instrumentation (not shown). An end 103 of the case 95 opposite the cable 102 has a curved shape geometrically matched with the alignment line 93 on the pad 61. Depicted on the top surface 90 is connector indicia in the form of an arrow 105 pointing from the reference connector contact 96 toward the detector connector contacts 97.

The electrode 61, 62 is used in the same manner as described above for the electrode 11. During assembly of the pad 61 and connector 62, proper mating engagement between the connector contacts 96, 97 and, respectively, the signal coupling surfaces 81–83 is achieved by aligning the curved end 103 of the connector 62 with the alignment line 93 on the pad 61. Again, either the tab 91 on the pad 61 or the arrow 105 on the connector 62 can be used to properly orient the electrode 61, 62 with respect to a bundle of muscle fibers.

Another biomedical electrode embodiment 111 is illustrated in FIG. 12. A flexible molded case 112 has a bottom surface 113 formed by an adhesive substrate. Retained by the case 112 is a linear array of contacts including a reference contact 115 and a pair of detector contacts 116. Each of the detector contacts 116 includes a rectangular block 117 as shown in FIG. 13. Outer elongated, planar surfaces 118 of the detector contact blocks 116 are orthogonal to the linear array and substantially aligned with the bottom substrate surface 113 of the case 112. Also included in each detector contact 116 are electrically conductive bristles 121 which project from the outer surface 118. The reference contact 115 also includes electrically conductive bristles 126 projecting from an outer elongated block surface 127 aligned with the substrate surface 113. However, again the reference surface 127 has an area substantially equal to the sum of the detector surfaces 118. The case 112 retains a flexible preamplifier 122 that is connected between the contacts 115, 116 and a cable 124 for connection to instrumentation (not shown). Imprinted on a top surface of the case 112 is orientation indicia in the form of an arrow 131 pointing from the reference contact 115 toward the detector contacts 116.

The electrode embodiment 111 is used in a manner similar to that described above for the embodiments 11 and 61, 62. However, in this case the adhesive substrate 113 of the flexible case 112 is adhered directly in a contoured fit to the skin covering a bundle of muscle fibers 55 as shown in FIGS. 6 and 7. Again, the arrow 131 is used to properly orient the electrode 111 with respect to the muscle fibers. The conductive bristles 121, 126 of, respectively, the detector contacts 116 and the reference contact 115 penetrate between any existing body hair to insure good electrical contact with the skin. Accordingly, valid diagnostic signal information can be derived with the unitary flexible case component 112.

Figure 14:
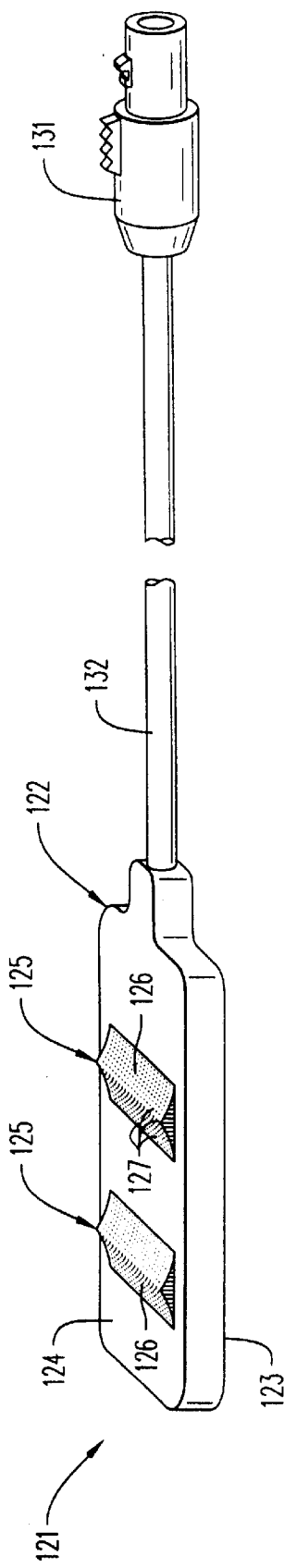
FIG. 14 is a perspective view of another biomedical electrode.
Figure 15:
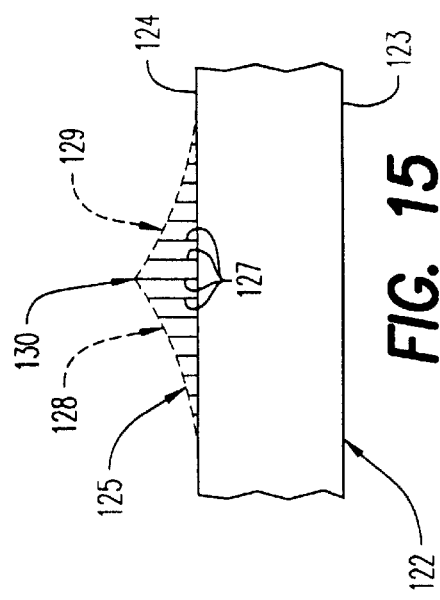
FIG. 15 is a partial side view of the electrode shown in FIG. 14.

FIGS. 14 and 15 illustrate another biomedical electrode embodiment 121. An injection molded case 122 retains a preamplifier (not shown ) and has a top surface 123 and a bottom surface 124. Covering the bottom surface 124 is a suitable adhesive substance for securing the case to the skin of a test subject. A pair of parallel, elongated contacts 125 have base portions retained by the case 122 and an outer portion 126 extending transversely to the bottom surface 124. Forming each of the contacts 125 are a bundle of electrically conductive bristles 127. Outer ends of the bristles 127 define a pair of concave surfaces 128, 129 intersecting along a longitudinal axis 130 of the contact 125. Each of the surfaces 128, 129 extend inwardly from the axis 130 toward the bottom surface 124. Preferably, each of the concave surfaces 128, 129 forms a catenary curve. Connecting the case 122 to a plug 131 is a wiring harness 132. The contoured bristle contacts 125 equalize tension when secured to skin and allow an accumulation of moisture between the bristles 127 thereby reducing impedance and minimizing the effect of changes in contact pressure between the bristles and skin as the electrode 121 is moved.

Figure 16:
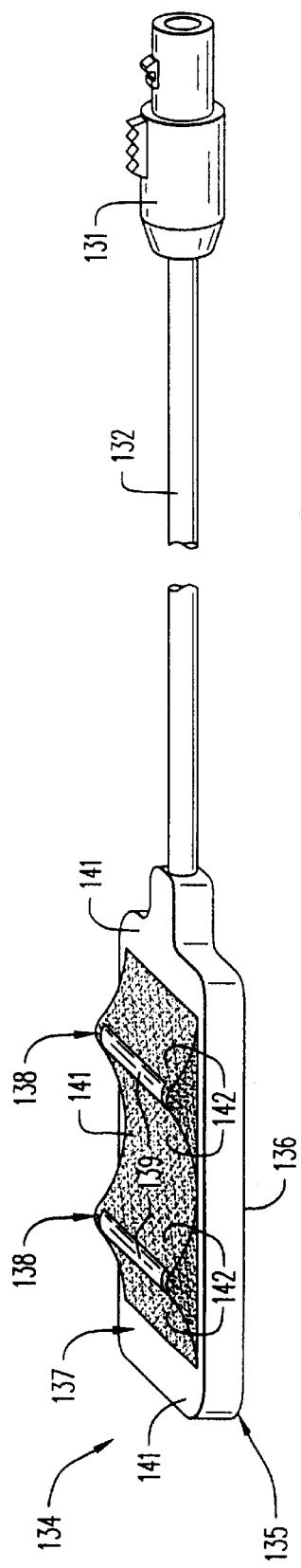
FIG. 16 is a perspective view of another biomedical electrode embodiment.
Figure 17:
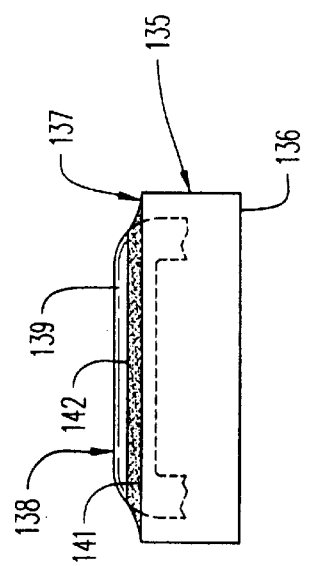
FIG. 17 is an end view of the electrode shown in FIG. 16.

FIGS. 16 and 17 illustrate another biomedical electrode embodiment 134. An injection molded case 132 retains a preamplifier (not shown) and has a top surface 136 and a bottom surface 137 covered with a suitable adhesive for securing the case 135 to the skin of a test subject. A pair of elongated and parallel cylindrical contacts 138 are retained by the case 135 and project outwardly from the bottom surface 137. Each contact 138 has an outer surface portion 139 for contacting the skin after attachment of the electrode 134. Included in the bottom surface 137 is a base portion 141 inwardly displaced from the outer contact surface portions 139 and concave transition portions 142 extending between the base portion 141 and opposite edges of the outer surface portions 139 of each contact 138. A wiring harness 132 connects a plug 131 to the case 135. Preferably, each of the transition portions 142 forms a catenary curve to minimize the skin tensioning effect of the protruding contacts 138. In addition, the transition portions 142 eliminate between the contacts 138 and the skin any cavities which can accumulate sweat and thereby reduce the period in which adhesion to the skin can be maintained.

Figure 18:
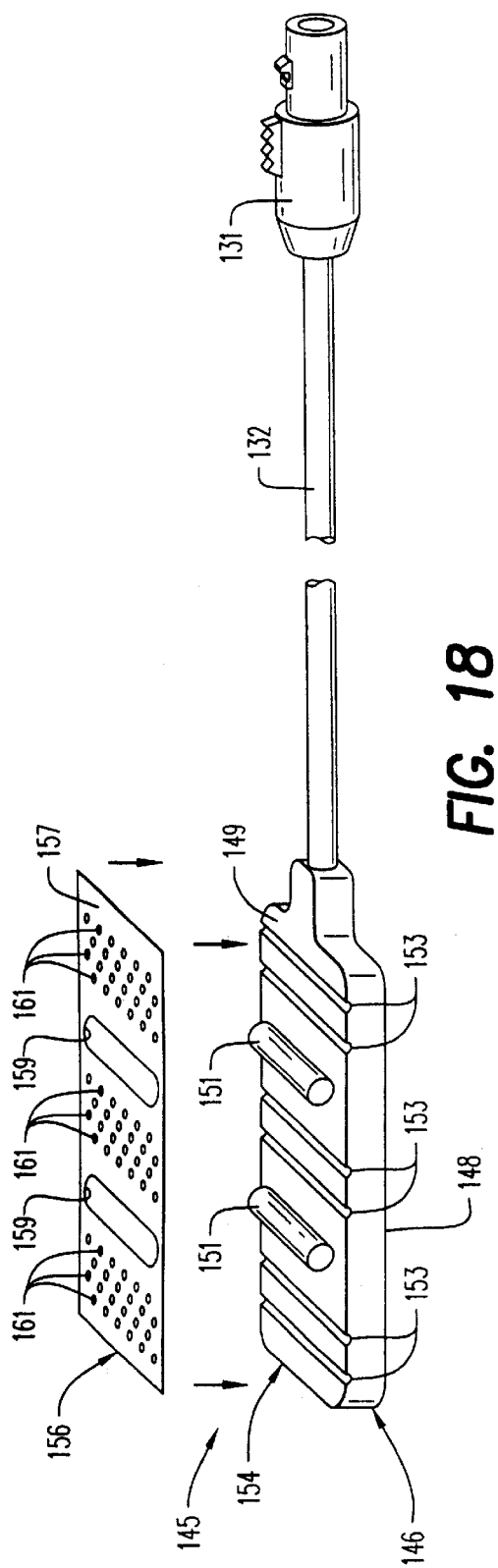
FIG. 18 is an exploded perspective view of another biomedical electrode embodiment.

Illustrated in FIG. 18 is another biomedical electrode embodiment 145. A molded case 146 retains a pre-amplifier (not shown) and has a top surface 148 and a bottom surface 149. Retained by the case are a pair of elongated, parallel and cylindrical contacts 151 projecting outwardly from the bottom surface 149. A wiring harness 132 connects the case 146 to a plug 131. Defined by the bottom surface 149 are a plurality of recess grooves 153 extending parallel to the contacts 151 and between opposite positions at the perimeter 154 of the bottom surface 149.

Also included in the electrode embodiment 145 is an attachment interface 156 covering the bottom surface 149 and having an adhesive surface 157 for securing the case 146 to the skin of a test subject. The interface 156 defines a pair of apertures 159 disposed to receive the contacts 151. Also defined by the interface 156 are a plurality of spaced apart openings 161 juxtaposed to and in communication with the grooves 153. During use of the electrode 145, the grooves 153 and openings 161 provide passages for escape of excess moisture and thereby prevent a premature failure of the adhesive on the surface 157 of the interface 156.

Figure 20:
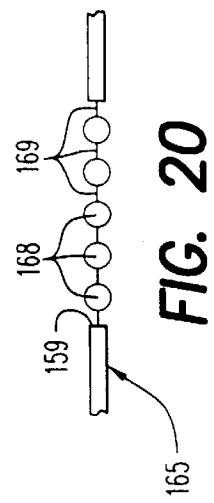
FIG. 20 is a partial cross-section of the interface shown in FIG. 19.
Figure 19:
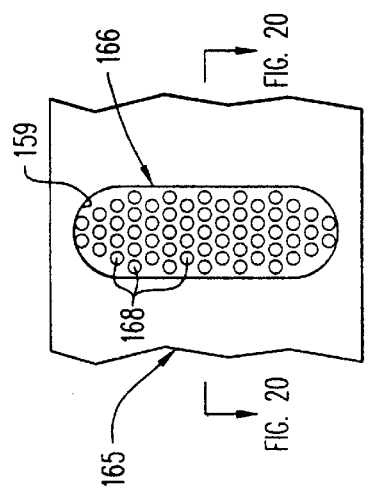
FIG. 19 is a top view of a modified adhesive interface for the electrode embodiment shown in FIG. 18.

Partially shown in FIGS. 19 and 20 is a modified attachment interface 165 for use with the electrode 145 depicted in FIG. 18. Covering each of the apertures 159 of the interface 165 is a flexible container pad 166. Each pad 166 is formed by an array of transversely spaced apart rupturable capsules 168 filled with electrolytes. The capsules 168 are retained by a flexible fiber matrix 169. During attachment of the interface 165 to the skin of a test subject, the capsules 168 are crushed and rupture to release their electrolyte contents in the regions between the skin and the contacts 151 and thereby enhance conductivity therebetween.

Obviously, many modifications and variations of the present invention are possible in light of the above teachings. It is to be understood, therefore, that the invention can be practiced otherwise than as specifically described.

What is claimed is:

1. A biomedical electrode comprising:
  a non-conductive case having a top surface and a bottom surface for attachment to the skin;
  an adhesive substance covering a portion of said bottom surface;
  a plurality of contacts retained by said case and projecting outwardly from said bottom surface, each of said contacts having an outer surface portion for contacting the skin; and wherein said bottom surface comprises a base portion inwardly displaced from said outer surface portions and transition portions sloping between said base portion and each of said outer surface portions.

2. A biomedical electrode according to claim 1 wherein each said outer surface portion is elongated with a pair of longitudinal edges at least one of which is intersected by one of said transition portions.

3. A biomedical electrode according to claim 2 wherein said elongated surface portions are arranged in a substantially parallel array disposed substantially parallel to said base portion.

4. A biomedical electrode according to claim 3 wherein each of said transition portions is concave.

5. A biomedical electrode according to claim 4 wherein each of said transition portions forms a catenary curve.

6. A biomedical electrode according to claim 3 wherein each of said contacts is cylindrical and disposed substantially parallel to said base portion.

7. A biomedical electrode according to claim 6 wherein each of said transition portions is concave.

8. A biomedical electrode according to claim 7 wherein each of said transition portions forms a catenary curve.

9. A biomedical electrode according to claim 2 wherein each of said edges is intersected by one of said transition portions.

10. A biomedical electrode according to claim 9 wherein said elongated surface portions are arranged in a substantially parallel array disposed substantially parallel to said base portion.

11. A biomedical electrode according to claim 10 wherein each of said transition portions is concave.

12. A biomedical electrode according to claim 11 wherein each of said transition portions forms a catenary curve.

13. A biomedical electrode according to claim 9 wherein each of said contacts is cylindrical and disposed substantially parallel to said base portion.

14. A biomedical electrode according to claim 10 wherein said elongated surface portions are arranged in a substantially parallel array disposed substantially parallel to said base portion.

15. A biomedical electrode according to claim 9 wherein each of said transition portions is concave.

16. A biomedical electrode according to claim 12 wherein each of said transition portions forms a catenary curve.

17. A biomedical electrode according to claim 1 wherein each of said transition portions is concave.

18. A biomedical electrode according to claim 14 wherein each of said transition portions forms a catenary curve.

19. A biomedical electrode according to claim 15 wherein each of said contacts is cylindrical and disposed substantially parallel to said base portion.

* * * * *